United States Patent
Moscetta

(10) Patent No.: US 9,927,418 B2
(45) Date of Patent: Mar. 27, 2018

(54) DEVICE AND METHOD FOR THE DETERMINATION AND MONITORING OF WATER TOXICITY

(71) Applicant: Pompeo Moscetta, Rome (IT)

(72) Inventor: Pompeo Moscetta, Rome (IT)

( * ) Notice: Subject to any disclaimer, the term of this patent is extended or adjusted under 35 U.S.C. 154(b) by 354 days.

(21) Appl. No.: 14/394,264

(22) PCT Filed: May 14, 2013

(86) PCT No.: PCT/IB2013/053911
§ 371 (c)(1),
(2) Date: Oct. 13, 2014

(87) PCT Pub. No.: WO2013/171667
PCT Pub. Date: Nov. 21, 2013

(65) Prior Publication Data
US 2015/0087011 A1     Mar. 26, 2015

(30) Foreign Application Priority Data
May 15, 2012 (IT) .............................. RM2012A0218

(51) Int. Cl.
G01N 33/18 (2006.01)
C12Q 1/18 (2006.01)
G01N 35/02 (2006.01)

(52) U.S. Cl.
CPC ........... G01N 33/1866 (2013.01); C12Q 1/18 (2013.01); G01N 35/025 (2013.01)

(58) Field of Classification Search
CPC ............ G01N 33/1866; G01N 35/025; G01N 35/0099; G01N 35/1004; G01N 35/1065; G01N 2001/007; G01N 2021/6482; G01N 2035/00168; G01N 2035/00287; G01N 2035/00356; G01N 2035/00475;
(Continued)

(56) References Cited

U.S. PATENT DOCUMENTS 4,325,910 A * 4/1982 Jordan ................. G01N 21/253
250/564
5,147,610 A * 9/1992 Watanabe ............. G01N 35/025
134/155
(Continued)

FOREIGN PATENT DOCUMENTS

| EP | 0682244 | 11/1995 |
| EP | 1883808 | 2/2008 |
| WO | 2006/125954 | 11/2006 |

OTHER PUBLICATIONS

International Search Report dated Jul. 25, 2013 for PCT/IB2013/053911, filed on May 14, 2013 in the name of Pompeo Moscetta.
(Continued)

*Primary Examiner* — William H. Beisner
*Assistant Examiner* — Danielle B Henkel
(74) *Attorney, Agent, or Firm* — Steinfl + Bruno LLP

(57) ABSTRACT

A device for analysis and monitoring of toxicity in waters is described. The device is specifically devised for determining toxicity in waters in several samples at the same time and in quick time with a high degree of accuracy and precision. The device has application in the field of controlling and monitoring the water resources and in the field of the ecotoxicological analyses.

10 Claims, 7 Drawing Sheets

(58) Field of Classification Search
CPC . G01N 2035/00752; G01N 2035/0405; G01N 2035/0436; G01N 2035/0441; G01N 2035/0444; G01N 2035/0446; G01N 2035/0453; G01N 2035/0465; G01N 2035/1025; G01N 2035/1076; G01N 2035/1086; G01N 2035/00386; G01N 2035/00455; G01N 2035/0443; G01N 2035/0448; G01N 21/03; G01N 21/6428; G01N 21/6452; G01N 21/76; G01N 33/53; G01N 33/5302; G01N 33/537; G01N 33/538; G01N 33/542; G01N 33/54313; G01N 35/0092; G01N 2035/00495; G01N 2035/0052; G01N 2035/0093; C12Q 1/18; B01F 11/0022; B29C 45/00; H01J 49/04; Y10T 436/11; Y10T 436/113332; B01L 2200/142; B01L 3/5025; B01L 3/50853; B01L 3/08; B01L 3/5085; B01L 9/06; B01L 2300/042; B01L 2300/043; B29K 2995/0032; B29L 2023/22

See application file for complete search history.

(56) References Cited

U.S. PATENT DOCUMENTS 5,840,572 A * 11/1998 Copeland ............ G01N 33/1866
356/427

6,190,617 B1   2/2001   Clark et al.
2001/0026936 A1   10/2001   Park et al.

OTHER PUBLICATIONS

Written Opinion dated Jul. 25, 2013 for PCT/IB2013/053911, filed on May 14, 2013 in the name of Pompeo Moscetta.

P. Bonini, et al., "Selectivity and random-access in automatic analysers", Journal of Automatic Chemistry, vol. 10, Nr. 4, 1988, pp. 167-170.

Jang-cheon Cho, et al., "A novel continuous toxicity test system using a luminously modified freshwater bacterium", Biosensors and Bioelectronics, vol. 20, nr. 2, 2004, pp. 338-344.

E. Kuster, et al., "On line biomonitors used as a tool for toxicity reduction evaluation of in situ groundwater remediation techniques", Biosensors and Bioelectronics, vol. 19, nr. 12, 2004, pp. 1711-1722.

J.H. Lee, et al., "Application of a multi-channel system for continuous monitoring and an early warning system", Water Science & Technology, vol. 53, No. 4-5, 2006, pp. 341-346.

R.N. Singh, et al., "Development of suitable photobioreactor for algae production—A review", Renewable and Sustainable Energy Reviews, vol. 16, No. 4, 2012, pp. 2347-2353.

* cited by examiner

DEVICE AND METHOD FOR THE DETERMINATION AND MONITORING OF WATER TOXICITY

CROSS REFERENCE TO RELATED APPLICATIONS

The present application is the US national stage of International Patent Application PCT/IB2013/053911 filed on May 14, 2013 which, in turn, claims priority to Italian Patent Application RM2012A000218 filed on May 15, 2012.

The present invention relates to a device for analysis and monitoring of toxicity in waters. The apparatus of the present invention is specifically devised for determining the toxicity in waters in several samples at the same time and in quick time with a high degree of accuracy and precision. The device of the present invention has application in the field of controlling and monitoring the water resources and in the field of the ecotoxicological analyses.

STATE OF PRIOR ART

The monitoring of quality in waters represents a fundamental issue for protecting safety and health worldwide. One of the technologies, very widespread worldwide for the water toxicological analysis, is a laboratory product sold under the commercial name of MicroTOX®, commercialized by Strategic Diagnostics Inc. This system is constituted by a luminometer used for measuring bioluminescence variations of bacteria rehydrated from lyophilized lots before the analytical tests. The analytical tests are performed in fully manual mode by specialized operators.

As far as monitoring of toxicity in waters through automated systems is concerned, only analyzers based upon flow technologies are commercially available. Some of the toxicity analyzers through bacterial organisms based upon flow technologies are TOXcontrol® On-line Biomonitor System, produced by microLAN B.V. and CCB-TOX® Continuous Contamination Biomonitor, produced by CheckLight Ltd. In brief, the sample and the luminescent bacteria are conveyed separately and introduced jointly into a chamber for measuring the luminescence for determining the sample toxicity effect. Immediately before and after it, the luminescent bacteria are conveyed separately and introduced together with the reference sample into a chamber for measuring the luminescence for determining the blank, parallel to the chamber for measuring the sample. The comparison between the blank and the sample shows the toxicity measurement.

Even as far as the monitoring of toxicity in waters with microalgae through automated systems is concerned, only analyzers based upon flow technologies are commercially available. The analyzer Algae Toximeter® is very widespread, produced by bbe-Moldaenke GmbH, wherein the microalgae are grown continuously in a fermenter. Like for flow systems based upon bacterial substrates, the analytical procedure is based upon the hydraulic conveyance of the biosubstrate in measurement chamber alternatively with blanks and samples and the result is obtained from the comparison of measurements of blank and sample. The monitored phenomenon is the algal delay in the light emission, better known as delayed fluorescence, caused by phytotoxic interfering substances.

An on-line analyzer produced recently is VibrioTox® of AppliTek, commercial derivation of patent EP1883808 (A2) of Gibson and Jones. This proprietary technology is based upon the monitoring of toxicity in waters through the use of bioluminescent bacteria which are grown continuously by a bio-reactor working under stationary state conditions. The bacteria are subsequently taken from the bio-reactor to allow performing the analysis in continuous flow mode.

Jang-cheon Cho et al. (Biosensors and bioelectronics, vol. 20, nr. 2, 2004) describe a device wherein recombinant bioluminescent bacteria in microplate are used for analyzing toxicity of aqueous samples. The device described in this document is not based upon the random access technology (Journal of Automatic Chemistry, Vol. 10, Nr. 4 (October-December 1988), p. 167-170). Eberhard kuster et al. (Biosensors and bioelectronics, vol. 19, nr. 12, 2004) describe a device for measuring toxicity in aqueous samples through bioluminescent bacteria *Vibrio fischeri*, this device too is not based upon the random access technology, but upon the flow technology already described above for the analyzer Algae Toximeter®.

MAIN ADVANTAGES OF PRIOR ART

One of the main limits of the prior art analyzers is the impossibility of analyzing several samples simultaneously and obtaining several measurements of the same sample with a high precision and accuracy level. Furthermore, the analyzers available in the prior art involve time for performing the analysis not compatible with the rapid intervention need as in case of events of unexpected contamination of waterworks.

The automatic analyzers existing in the prior art are based upon the hydraulic handling of microorganisms (algae and bacteria) and therefore are subject to cross-contamination and to fouling.

Object of the Invention

The present invention relates to a device, based upon random access technology with direct reading, to monitor autonomously and continuously the quality of waters and to analyze in automated way samples, leachates and aqueous extracts, including the component portions of the same, associated to analytical methods allowing to determine the contamination in waters and detect the presence of contaminants in samples, leachates and aqueous extracts.

The device of the present invention is applied in the field of controlling and monitoring the water resources, including waterworks and groundwater, waters for industrial use inletting and outletting from plants, civil and industrial pre-treated and after-treated refluent waters, groundwaters and surface waters, including streams, sources, brooks, channels, water basins, rivers, lakes and including sea waters too. Analogously the invention can be used in the field of the ecotoxicological analyses on samples, leachates and aqueous extracts of any origin and/or derivation, including waste, soils, sediments and materials.

The object of the present invention is to solve the several problems still left opened by the known art and this is obtained through a device as defined in claim 1.

Additional features of the present invention are defined in the corresponding depending claims.

Advantages of the Invention

The present invention, by overcoming the mentioned problems of known art, involves several and evident advantages:

1. Possibility of continuos monitoring.
2. Possibility of sampling and processing tens of samples simultaneously.
3. Very reduced time for sampling, preparation and measurement.
4. Complete analytical autonomy with safeguarding of costs and workforce.
5. More experimental accuracy and precision.
6. Signalling in almost real time, even remotely, unexpected events of contamination and consequent possibility of timely making safe the monitored water resource, water body, refluent substance, effluent or waterworks.
7. Possibility of evaluating simultaneously the toxicity effects on bacteria and algae, that is prokaryotic and eukaryotic organisms, with time of usability, stability and duration of the microbic substrates which can be quantified in a range comprised between 25 and 35 days.

Whereas the devices (analyzers) with flow technologies of known art allow analyzing one sample only or however a very limited number of samples at a time, the device of the present invention allows the simultaneous analysis of a high number of samples, equal to the positions available in the reaction tray. Therefore, there is also the possibility of performing simultaneous repetitions of the same sample, analyzing at the same time the same sample with different dilutions and performing contemporarily measurements of blank and calibration with pure compounds and/or real matrixes with known toxicity.

The device of the present invention allows analyzing a sample every 10-30 seconds, against the 15-30 minutes for each sample of the flow technologies.

The continuous passage of bacterial or algal suspensions along the whole path of the flow analyzers increases the risk of fouling and bio-fouling, especially in tubes and ducts. Therefore, one or more washing and sterilization procedures of the whole system between one sample and the other one are necessary, in order to avoid the already mentioned fouling or any type of interference with the subsequent analysis. On the contrary, in the herein described device, the collecting needle and the reaction cuvettes are exposed to potential contamination and therefore subjected to washing. This allows guaranteeing a very high level of cleaning and reliability of the system.

The flow analyzers can perform measurements in simultaneous kinetics of blanks, calibrators and samples only if equipped with multiple detectors, in a number equal to the blanks, calibrators and samples to be measured contemporarily. However, performing the measurements of blanks, calibrators and samples in different periods of time causes errores which can become significant, given that the toxicity effect is calculated by the signal decrease or variation, observed with respect to a test performed in absence of contamination. Consequently, the obtained result is strictly linked to the ideal metabolic activity of the active population which can be expressed in that precise time range. Given the innate transitoriness of the metabolic status thereof, both the bacteria and the microalgae can be subjected to signal variations and sensibility even very significant with the time elapse. On the contrary, the device of the present invention simultaneously can perform measurements in kinetics of blanks, calibrators and samples, event at very reduced intervals, such as every 10-30 seconds, for the whole wished time, by using one single bioluminescence detector and one single fluorescence detector, as it is the reaction tray to rotate and place in the position corresponding to the requested detector. This results to be an essential added value, which allows performing, in parallel to the analyses of real samples, cycles of blanks and calibrations with known solutions of different types of toxic analytes and/or real matrixes with known toxicity.

With respect to the analyzer VibrioTox® of AppliTek, the device object of the present invention, has the following additional advantages:
1. The biological reactive contained in disposable small phials is monitored by means of operation of blanks and contaminants. In case of efficiency loss, the reactive can simply be replaced. On the contrary, in the device VibrioTox®, the chemostat is a fermenter with very critical management and easily subject to outer contamination and it requires, to be kept in operation in an efficient way, complex controls of innumerable parameters, such as the density of microorganisms, the total volume, the addition and removal of reagents, aeration and turbidity. In case of contamination of simple failure or inconvenience, the re-activation of the fermentation cycle is a long and complicated procedure or at least not so immediate like the replacement of a small phial.
2. Being subject to the formation of small air bubbles difficult to be removed, which can influence sensibly the analytical measurement, the hydraulic system of the flow analyzers needs air traps or analogous systems for removing such bubbles.
3. The luminescence or fluorescence measurement in a continuous flow analyzer has necessarily very accelerated timing as the biologic analytes are suspended in a moving fluid. Furthermore, the number of measured photons varies depending upon the flow speed. Considering that in the herein described device the reading takes place under static conditions, it results to be more robust and repeatable.
4. In an analyzer with continuous flow, the analytical sensibility is lower due to the reduced volumes which can be read by the detector. This problem is physiological to the type of analyzer considering that, in order to increase volumes, it would be essential reducing the flow speed, with consequent unacceptable unbalances in the flow itself and fluctuations in the number of measured photons.

BRIEF DESCRIPTION OF THE DRAWINGS

FIG. 8 shows the zinc-inhibiting kinetics obtained by experimental way, as described in Example 2.

DETAILED DESCRIPTION OF THE INVENTION

Figure 1:
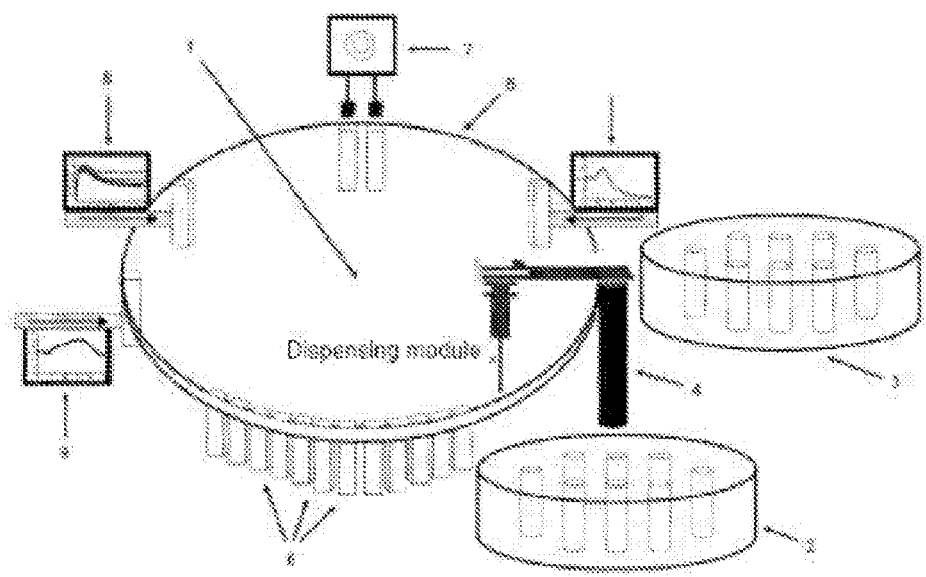
FIG. 1 is a schematic representation of an embodiment of the device according to the present invention.
Figure 2:
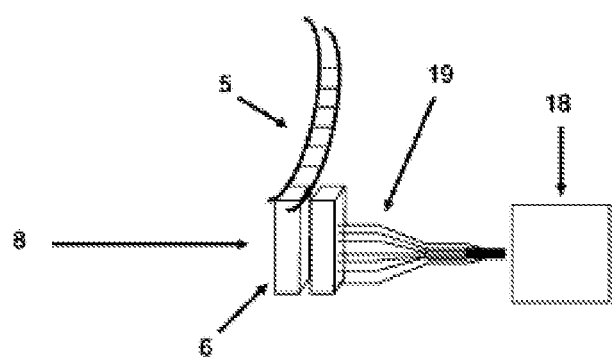
FIG. 2 is a detail of the luminometric measurement module 8 of the embodiment shown in FIG. 1.
Figure 3:
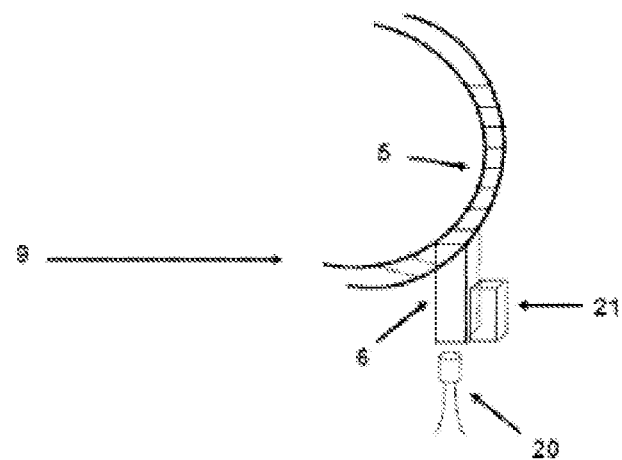
FIG. 3 is a detail of the fluorimetric measurement module 9 of the embodiment shown in FIG. 1.

The present invention has as object a device 1 for the analysis and the monitoring of toxicity in waters based upon the technology known as random access described in Journal of Automatic Chemistry, Vol. 10, Nr. 4 (October-December 1988), p. 167-170, and incorporated herein by reference comprising:

a) an aqueous sample storage module 2;
b) an aqueous buffer storage module 3;
c) a dispensing module 4;
d) a reaction tray 5 apt to accommodate reaction cuvettes 6;
e) a washing module 7 of said reaction cuvettes 6;
f) one or more luminometric measurement modules 8 and/or fluorimetric modules 9 arranged at predefined positions of said reaction tray 5.

The dispensing module 4 is mainly a module for collecting, transferring and adding reagents and samples and it could comprise a mechanical arm preferably equipped with 3 degrees of freedom, sensor with capacitive level, preheating of reagents with programmable temperature, needle with automatic inner and outer washing, automatic predilution of reagents and samples with sampling interval preferably comprised between 3 and 330 microliters and pitch comprised between 0.25 and 1.00 microliters.

The reaction tray 5 is a tray equipped with housing for the reaction cuvettes 6 containing the sample to be analyzed. The tray could be arranged for housing a high number of cuvettes, such as example 50, 60, 70, 80, 100 with different volume, for example 500 microliters. In a preferred embodiment, the tray is equipped with the possibility of adjusting the reaction temperature, for example in a range comprised between 10 and 50° C., by means of circulating liquid in suitable channel implemented in the tray body.

The washing module of the reaction cuvettes 7 preferably will be connected to containers containing washing solutions and programmable to perform autonomously the number of washing and sterilization cycles requested by the operator. The washing module will be for example positioned on the periphery of the reaction tray and it will access the cuvettes of the tray through a vertical translation. The washing module preferably will also be a sterilization module; in this case suitable sterilization solutions will be used. The washing module 7 preferably will comprise a specific drainage line to drain washing.

The aqueous sample storage module 2 is a module containing the samples, leachates or aqueous extracts to be analyzed. In an embodiment, the module is structured so as to be able to house preferably at least 4 baskets handled by 15 positions, each one containing 3 ml, and 8 fixed containers, each one containing 3 ml.

The aqueous buffer storage module 3 is a compartment for storing the dilution buffers and rehydration solutions suitable to rehydrate or dilute the microorganisms used for the toxicological analysis. In an embodiment, the module preferably includes at least two motorized baskets with 16 positions for 20-mL phials and preferably at least 4 fixed cylindrical 50-mL containers. The storage module could contain a thermostat for adjusting the temperature thereof.

The device 1 could comprise one or more luminometric 8 and/or fluorimetric 9 measurement modules.

In an embodiment, the luminometric measurement module 8 comprises a photomultiplier 18 and an optical fiber bundle 19 arranged at a predefined position of said reaction tray 5. The optical fiber bundle 19 has a rectangular section and a surface substantially corresponding to the surface of said reaction cuvettes 6 from the side of said reaction tray 5 and a circular section from the side of said photomultiplier 18; this embodiment allows obtaining better analytical results, in particular when the optical fibres have sizes comprised between 100 and 150 $mm^2$ and preferably about 130 $mm^2$.

In an embodiment, the fluorimetric measurement module 9 comprises at least 3 excitation light sources 20 with different wavelength and the respective detectors 21 are placed at about 90° with respect to said light sources.

Figure 4:
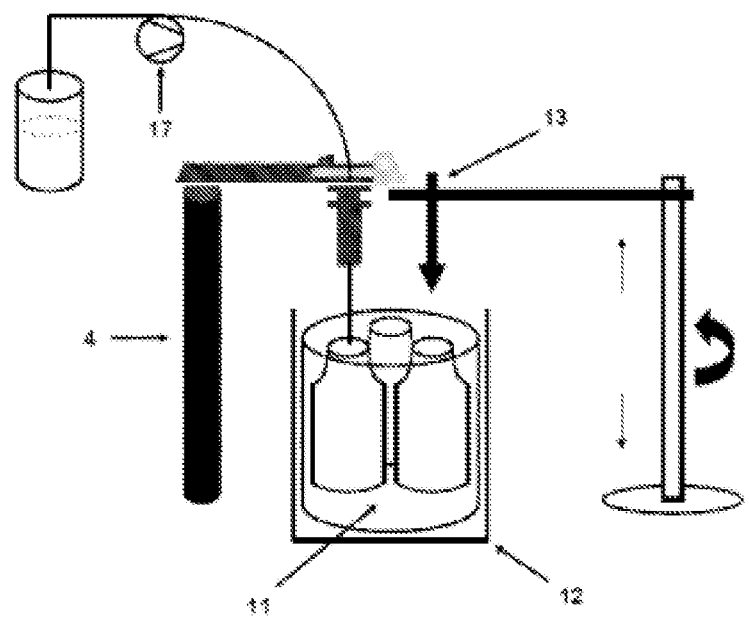
FIG. 4 is a schematic representation of an embodiment of the microorganism rehydration module.

In an embodiment, the device 1 comprises a module for rehydrating microorganisms. By making reference to FIG. 4, the rehydrating module in a preferred embodiment is based upon a basket 11 for housing phials containing the lyophilized microorganisms; the phials, for example, could have a volume of about 20-25 ml to allow inletting the rehydration buffer. The basket 11 is contained inside a refrigerated mantle 12 with controlled temperature, for example 4° C., and it is shrunk on a motorized small shaft which can allow the rotation of the phials both with the purpose of mixing the suspension of microorganisms and positioning the same below the extraction device 13 of the rubber closing plug and allow then the automatic rehydration of the microorganisms. The extraction device 13 could have the shape of a pawl for penetrating in the rubber plug with a translation downwards and the removal of the same with a translation upwards. Once removed the plug, the phial-holding basket 11 is properly rotated for positioning the phial below the dispensing module 4. The dispensing module 4 could be then equipped with a supplying cannule connected to a mini-pump 17 suitable to the transfer of the rehydration buffer from the specific container to the phial to be rehydrated.

Figure 5:
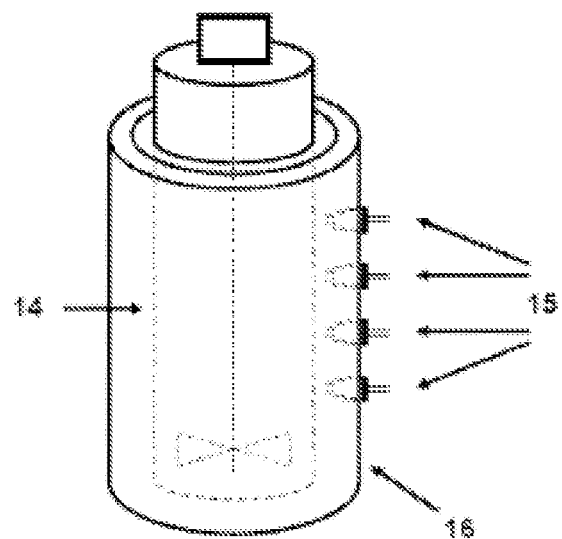
FIG. 5 is a schematic representation of an embodiment of the thermostated and lighted reactor for the supporting of algal solutions.

In an embodiment, the device comprises a thermostated and lighted reactor for the supporting of algal solutions. By making reference to FIG. 5, the thermostated and lighted reactor for the supporting of algal solutions in a preferred embodiment comprises a test tube 14 with great sizes, for example made of glass, with a volume of about 100 ml, wherein the algal suspension is reconstituted to be kept herein for a period of about 30 days. The glass test tube is inserted inside a thermostated mantle at a temperature of about 25° C. On the mantle wall a series of holes is implemented to house as many LED diodes to light the solution constantly. A plug is positioned in the test tube upper end whereon a small engine is fastened for the rotation of a small shaft whereon a helix mixer is shrunk, necessary to keep the microalgae in suspension. From the same closing plug it is possible accessing inside the test tube with the sucking/dispensing needle existing on the dispensing module, both for collecting the algal suspension necessary for the analysis and for introducing periodically a nourishment solution, which is kept in the reagent department.

The presence of the thermostated and lighted reactor allows using algal solutions for measuring toxic substances, such as herbicides, heavy metals, etc. The algal solutions must be kept alive at controlled temperature by lightening them with specific wavelengths and providing nutritional substance every day.

In an embodiment, the device 1 will comprise even one or more colorimetric measurement modules 10, arranged at predefined positions of said reaction tray 5. The colorimetric measurement module 10 could comprise, for example, a colorimeter, a spectrophotometer, a spectrophotometer with monocromator.

In an embodiment, the device 1 will comprise even means for controlling the operations of the different modules such as, for example, an electronic platform allowing to control all operating devices, the dialogue with the user interface software and the remote timely signalling via web or mobile phone of the obtained data and of any analytical or instrumental recorded anomalies. Said means for controlling the operations could comprise software and hardware for programming and executing in fully automated form the analytical cycles defined by the operator, such as for example, for executing end-point analyses, kinetics, fixed time, multistandard and differentials with blank sample, under luminescence and fluorescence, with the possibility of being able to associate thereto even the colometry sptrophotometric measurement. The various modules constituting the device could be controlled by a system with central microprocessor controlling the various phases of the analytical sequences. In particular the various detectors (Spectrophotometer, Colorimeter, Luminometer, Fluorimeter) will be arranged along the periphery of the reaction tray 5, which could be equipped with a handling system with stepper motor, allowing an accurate positioning of each cuvette in front of each detector.

In an additional embodiment, the device 1 could comprise a sampling module with means for the filtration, UV digestion, acid digestion, distillation, dialysis, dilution and/or concentration of the aqueous samples be analyzed. In order to monitor or analyze supply or drainage waters or coming from a surface or underground environmental water body, landfill leachates or aqueous extracts of soils, sediments and continuous materials, a sampling module is necessary. Some of these matrixes, thereamong the network waters and the effluent refluent substances, cannot be always analyzed directly considering that they are subjected to disinfecting treatments, such as chlorination, chloroamination, ozonation and peroxidation. For example, the residual level of dissolved free chlorine, generally comprised between 0.5 and 1.0 mg/L, which is kept in order to protect drinking water from bacterial contamination during the transfers, must be preliminarily demolished with a suitable removing agent.

An option usable in pre-treating the sample and provided, under the preferable but not necessary form, provides the prefiltration of the samples to be analyzed. It is useful to the purpose of removing suspended solids and, generically, substances apt to interfere with the analytical measurements. In addition, means for integrating a module for the preconcentration of the sample could be comprised, wherein it is necessary increasing the analytical sensibility and therefore lowering the measurable toxicity threshold. In a "laboratory" version of the device, a compartment is provided, in series, wherein the operator can house a high number of samples, coming from different sampling points, and which can have been pre-treated (filtered, distilled, etc.) in advance by the operator. In the "on-line" version, it is necessary to bring the sample to the analyzer or continuously or on the occasion of performing a new analysis cycle. Since the sample physical features (torbidity, presence of organic substance, etc.) could be not suitable for a direct transfer thereof in the analytical reactor, it becomes necessary interposing between the sample and the analyzer one or more sampling and pre-treatment modules, which could allow the sample preparation for the subsequent analysis. The pre-treated sample with one or more of the described modes is made to flow in as many small wells with overflow with constant volume, to be taken from the device in the suitable moment.

In an additional embodiment, the device 1 will comprise means for adjusting the temperature of the aqueous buffer storage module 3 and/or of the reaction tray 5. The cooling could be obtained through continuous passage of water refrigerated at the requested temperature, inside a specific channel implemented in the reaction tray body; the refrigerated water will be, for example pumped by an outer chiller. The heating could be obtained by interrupting the circulation of refrigerated water and feeding a heating band with adequate thermal power positioned on the base of the metallic body of the reaction tray.

It is also object of the present invention the use of the device in all possible embodiments described above in a process for analyzing and monitoring toxicity of an aqueous sample using bioluminescent bacteria and/or microalgae and said processes.

Preferably, the process for analysing acute toxicity according to the invention provides the use of bioluminescent bacteria belonging to the reference strain *Vibrio fischeri* NRRL B-11177. The bacteria are grown, stabilized and lyophilized so as to guarantee a continuing use thereof after rehydration in suitable saline buffer. In this way, they keep for 25-30 days a measurable bioluminescence signal and an unaltered sensibility to the different types of toxic compounds, which can be grouped in two big macro-categories: organic pollutants, thereamong pesticides and hydrocarbons, and inorganic pollutants, thereamong the heavy metals and anions such as cyanide.

Preferably, the process for quickly determining algal toxicity according to the invention provides the use of microalgae which, preferably but not necessarily, belong to the species *Chlamydomonas reinhardtii*. The microalgae are grown, stabilized and immobilized in original manner so as to guarantee a continuing use thereof after re-suspension in suitable saline buffer. In this way, they keep for 30-35 days an excitable and measurable variable relative fluorescence and an unaltered sensibility to the different types of toxic compounds, which can be grouped in two bid macro-categories: organic pollutants, thereamong the herbicides, and inorganic pollutants, thereamong the heavy metals.

The continuous measurement of blanks and samples with increasing concentrations and predefined time intervals, basically of 30 seconds, results in the generation of inhibition kinetics allowing to acquire preliminary information about the nature and the concentration of the contaminant influencing the bacterical bioluminescence and/or algal variable relative fluorescence signal.

By using the invention device it is also possible performing immediately repetitions, with equal or higher concentrations of sample, to confirm an identified toxicity or clarify, in positive or negative sense, a doubtful toxicity.

As mentioned previously, the parameter commonly used to define an acute toxicity measurement is the percentage inhibition. It represents the variation in the light emitted by the microorganisms in percentage points caused by the sample presence. The light emission of blank performed by using water or matrix with null toxicity instead of the sample is used as reference value.

For the bioluminescent bacteria the percentage inhibition ($IC_{b(t)}$ (%)) could be determined as shown hereinafter:

$IC_{b(t)}$ (%)=[1−($RLU_{S(t)}$/$RLU_{B(t)}$)]×100, wherein $IC_{b(t)}$ (%) is the bioluminescence percentage inhibition at time t induced by the sample S, $RLU_{S(t)}$ is the luminescence measurement of sample S at time t expressed in luminescence relative units RLU and $RLU_{B(t)}$ is the luminescence measurement of the blank B at time t expressed in luminescence relative units RLU.

For the microalgae:

$IC_{f(t)}$ (%)=[1−($RVF_{S(t)}$/$RVF_{B(t)}$)]×100, wherein $IC_{f(t)}$ (%) is the percentage inhibition at time t, $RVF_{S(t)}$ is the dimensionless measurement of variable relative fluorescence calculated for the sample S at time t and $RVF_{B(t)}$ is the is the dimensionless measurement of variable relative fluorescence calculated for the blank B at time t.

The aqueous samples are properly mixed with said microorganisms in wholly automated mode by means of discrete technology and said measurement stations are able to measure the photons emitted by said microorganisms under bioluminescence and/or fluorescence, therefore when, after the contact with said aqueous samples, said measurement stations record a significant variation in the number of emitted photons, the analyzer timely signals that said aqueous samples are contaminated.

The added substances (reaction buffers) in the herein described processes alter the ionic force of said aqueous samples, so as to make them isotonic for said microorganisms. Furthermore, said reaction buffers can be used to alter the ionic concentration of at least one selected ion and, more preferably, to remove toxic compounds generated after chlorination, chloroamination, ozonation or peroxidation of said supply or drainage water network or of said samples, leachates or aqueous extracts.

Said microorganisms are a population of bioluminescent bacteria and a population of microalgae stored in separate compartments. Said bioluminescent bacteria and said microalgae can be used each time in series or parallelly, both for monitoring waters and for analyzing said samples, leachates or aqueous extracts. More typically, said microorganisms are selected so that the sensibility thereof to the contaminants expresses through a significative variation in the photo-emitting capabilities thereof. In case of bacteria, this is specifically due to the decrease or death of a portion or of all the considered population, whereas in case of the microalgae this is specifically due to an interference to the normal process of chlorophyll photosynthesis.

In an alternative embodiment of the invention, it is possible that bacteria are used showing an increased light emission, in response to the presence of particular contaminants. In this case the bacterial population is able to detect the presence of bionutrients.

In an embodiment, in each position of the reaction tray 5, said microorganisms, alternatively bioluminescent bacteria or microalgae, are combined with one or more said aqueous buffers and with one or more said samples, leachates or aqueous extracts, in order to determine the presence of possible contaminants in said samples, leachates or aqueous extracts and all operations for adding and mixing said microorganisms, said aqueous buffers and said samples, leachates or aqueous extracts are performed automatically by the dispensing module based upon robotic technology. A luminometer and a fluorimeter are associated to fixed positions outside the reaction tray; the reaction tray 5 rotates automatically in order to position alternatively each reaction cuvette containing said microorganisms, said aqueous buffers and said samples, leachates or aqueous extracts at the height of the luminometer or the fluorimeter, in order to measure automatically the light emitted by the reaction suspension. After performing the measurements at preset time intervals and for the preset duration, all suspensions contained in said reaction cuvettes are removed and disposed of by means of suitable drainage line. The used positions are washed and sterilized automatically by said washing module.

The process according to an embodiment comprises the following passages defining a process for analyzing and monitoring continuously aqueous samples:

i. transferring aqueous samples from a water supply or drainage network or from a natural or artificial water body into a device of random access type ii. rehydrating one or more phials of microorganisms;

iii. metering water aliquots inside one or more cuvettes positioned on a rection tray;

iv. metering aliquots of said aqueous samples, in amounts analogous to said water aliquots added into said blank cuvettes, or in lesser volumes, followed by additions of complementary volumes of water, inside one or more sample cuvettes positioned on said reaction tray;

v. metering aliquots of one or more aqueous buffers inside said blank cuvettes and said sample cuvettes;

vi. metering aliquots of said microorganisms inside said blank cuvettes and said sample cuvettes;

vii. measuring at preset times, for a determined time interval under bioluminescence and/or fluorescence, the photons emitted by said blank cuvettes and by said sample cuvettes;

viii. detecting, where a significant change in light emission has been recorded as a result of the contact of said aliquots of said microorganisms with said aliquots of said aqueous samples, the presence of contaminants in said aqueous samples;

ix. removing and unloading said aliquots of said microorganisms, said aliquots of said aqueous buffers, said aliquots of water and said aliquots of said aqueous samples from said blank cuvettes and from said sample cuvettes; wherein said process is characterized in that the handling of said aliquots of said microorganisms, said aliquots of said aqueous buffers, said aliquots of water and said aliquots of said aqueous samples is autonomously and automatically managed by a mechanical arm equipped with 3 degrees of freedom preferably equipped with collection needle with capacitive level sensor.

The process according to an additional embodiment of the invention comprises the following passages defining an analytical method in batches to detect the presence of contaminants in samples, leachates and aqueous extracts:

i. introducing one or more samples, leachates and aqueous extracts inside a device of random access type;

ii. rehydrating one or more phials of microorganisms;

iii. metering water aliquots inside one or more blank cuvettes positioned on a reaction tray;

iv. metering aliquots of said samples, leachates or aqueous extracts, in amounts analogous to said water aliquots added into said blank cuvettes, or in lesser volumes, followed by additions of complementary volumes of water, inside one or more sample cuvettes positioned on said reaction tray;

v. metering aliquots of one or more aqueous buffers inside said blank cuvettes and said sample cuvettes;

vi. metering aliquots of said microorganisms inside said blank cuvettes and said sample cuvettes;

vii. measuring at preset times, for a determined time interval under bioluminescence and/or fluorescence, the photons emitted by said blank cuvettes and by said sample cuvettes;

viii. detecting, where a significant change in light emission has been recorded as a result of the contact of said aliquots of said microorganisms with said aliquots of said aqueous samples, leachates or aqueous extracts, the presence of contaminants in said samples, leachates or aqueous extracts;

ix. removing and unloading said aliquots of said microorganisms, said aliquots of said aqueous buffers, said aliquots of water and said aliquots of said samples, leachates or aqueous extracts from said blank cuvettes and from said sample cuvettes and repeating from the beginning the above-described process; characterized in that:

the handling of said aliquots of said microorganisms, said aliquots of said aqueous buffers, said aliquots of water and said aliquots of said samples, leachates or the aqueous extracts is autonomously and automatically managed by a mechanical arm equipped with 3 degrees of freedom preferably equipped with collection needle with capacitive level sensor.

Preferably but not necessarily, in both embodiments of the above-described processes, to each measurement of said sample, leachate or aqueous extract, a measurement of the related blank corresponds, performed by adding an equal or analogous quantity of water instead of the sample, leachate or extract itself. This is made possible by the intrinsic potentialities of the device based upon RA technology, which succeeds in preparing and measuring blanks and samples in sequence within few seconds. Furthermore, it is possible associating to the same blank measurement a series of measurements of sample with different dilutions in order to determine, with maximum accuracy, the level of toxicity induced by the sample on the selected microorganisms, that is the sample quantity necessary to reduce significantly the luminescence of bacteria and/or condition significantly the fluorescence emission after proper excitation by the microalgae, in a determined time interval. Furthermore, even the interval provided between a measurement and the other one of the same blank and sample can be accurately programmed in order to perform measurements of kinetic type and to calculate the time needed to contaminants to cause a significative reduction of the bacterial luminescence and/or a significative change in the algal fluorescence emission, that is to cause a measurable toxicity effect. The use of the discrete technology, then, allows the user to accumulate simultaneously and in almost real time, information correlating action times, concentrations and toxicity effects of contaminants both on prokaryotic and eukaryotic organisms, allowing both an on-line continuous monitoring of a same matrix and an in-batch screening with high performance of different samples, leachates or extracts.

Typically in the bacterial test, a bioluminescence reduction is observed when contaminants with toxic effect are contained in the aqueous sample and this reduction is defined percentage inhibition. The analytical result is expressed as IC 50 at a determined incubation time, that is the concentration of sample, leachate or aqueous extract or contaminant necessary to cause a bioluminescence reduction equal to 50 percent of the bioluminescence emitted by the blank after that same incubation time.

Typically in the algal test, a reduction in the variable relative fluorescence is observed, when contaminants with toxic effect are contained in the aqueous sample and this reduction is defined percentage inhibition. The analytical result is expressed as IC 50 at a determined incubation time, that is the concentration of sample, leachate or aqueous extract or contaminant necessary to cause a reduction in variable relative fluorescence equal to 50 percent of the variable relative fluorescence emitted by the blank after that same incubation time According to a preferred embodiment of the invention, the bioluminescent bacteria are provided under lyophilized form, they are rehydrated automatically and they are kept in a preserving solution convenient thereto in said module for the rehydration and storage of microorganisms.

According to a preferred embodiment of the invention, the microalgae are provided under immobilized form and they are resuspended automatically in suitable aqueous buffer and kept in a preserving solution convenient thereto in said module for the rehydration and storage of microorganisms.

According to a further preferred embodiment of the invention, the bioluminescent bacteria are kept under extremely slow-down growth conditions in order to keep at maximum level the reproducibility of the analytical performances. This is obtained by refrigerating at 4° C. a dedicated compartment of said module for the rehydration and storage of microorganisms by means of refrigeration circuit.

According to a further preferred embodiment of the invention, the microalgae are kept under optimum growth conditions in order to keep at maximum level the reproducibility of the analytical performances. This is obtained by conditioning at 24° C. a dedicated compartment of said module for the rehydration and storage of microorganisms by means of conditioning circuit.

EXAMPLES

By means of the device object of the present invention, the tests described in the examples were performed, according to one of the above-described processes. The following examples are illustrative only and they do not limit the invention.

Example 1—Toxicity Measurement of Phenol as Reference Organic Compound

Figure 6:
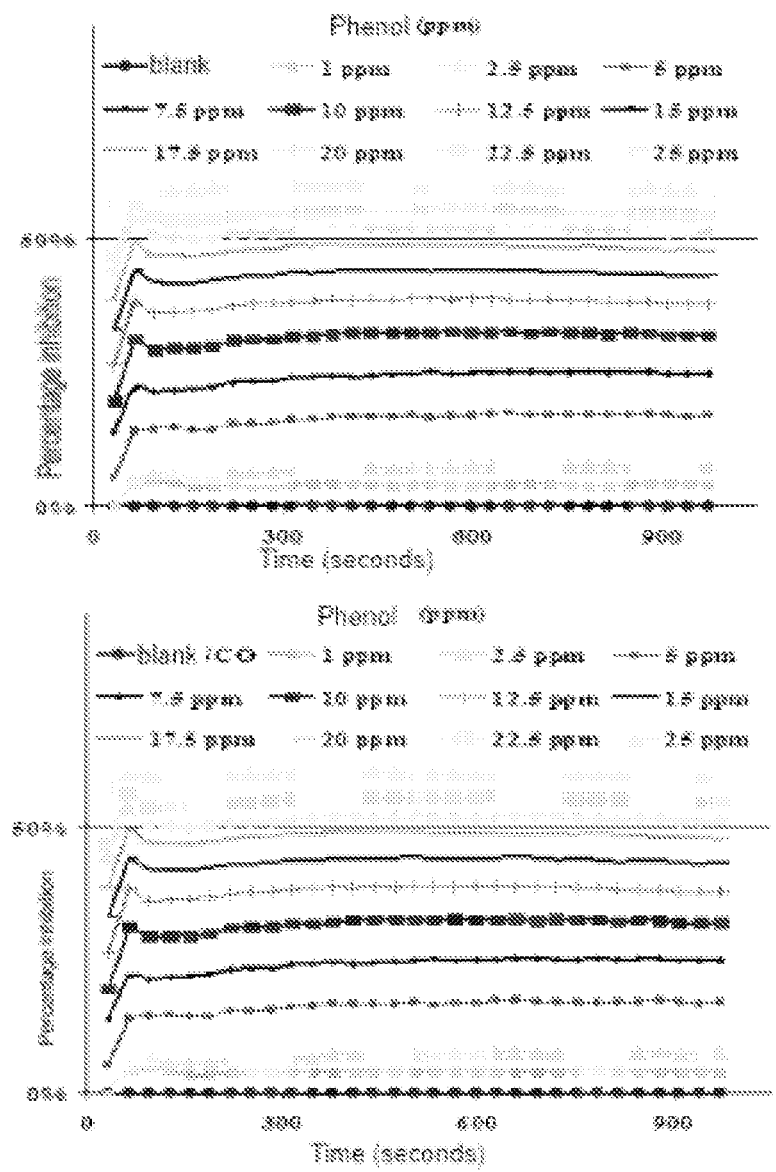
FIG. 6 shows the phenol-inhibiting kinetics obtained by experimental way, as described in the Example 1.
Figure 7:
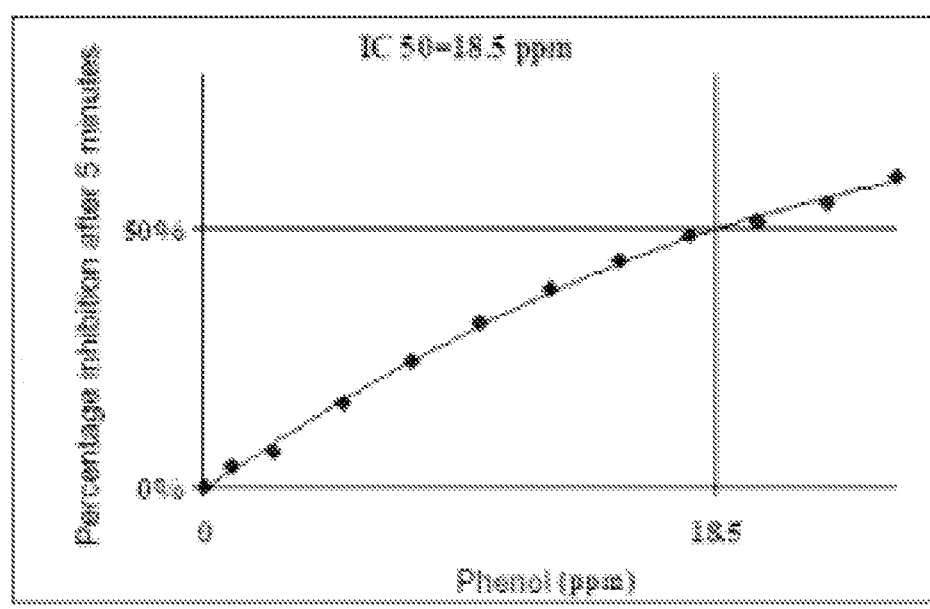
FIG. 7 shows the calculation of IC 50 obtained with the data of FIG. 6.
Figure 6:
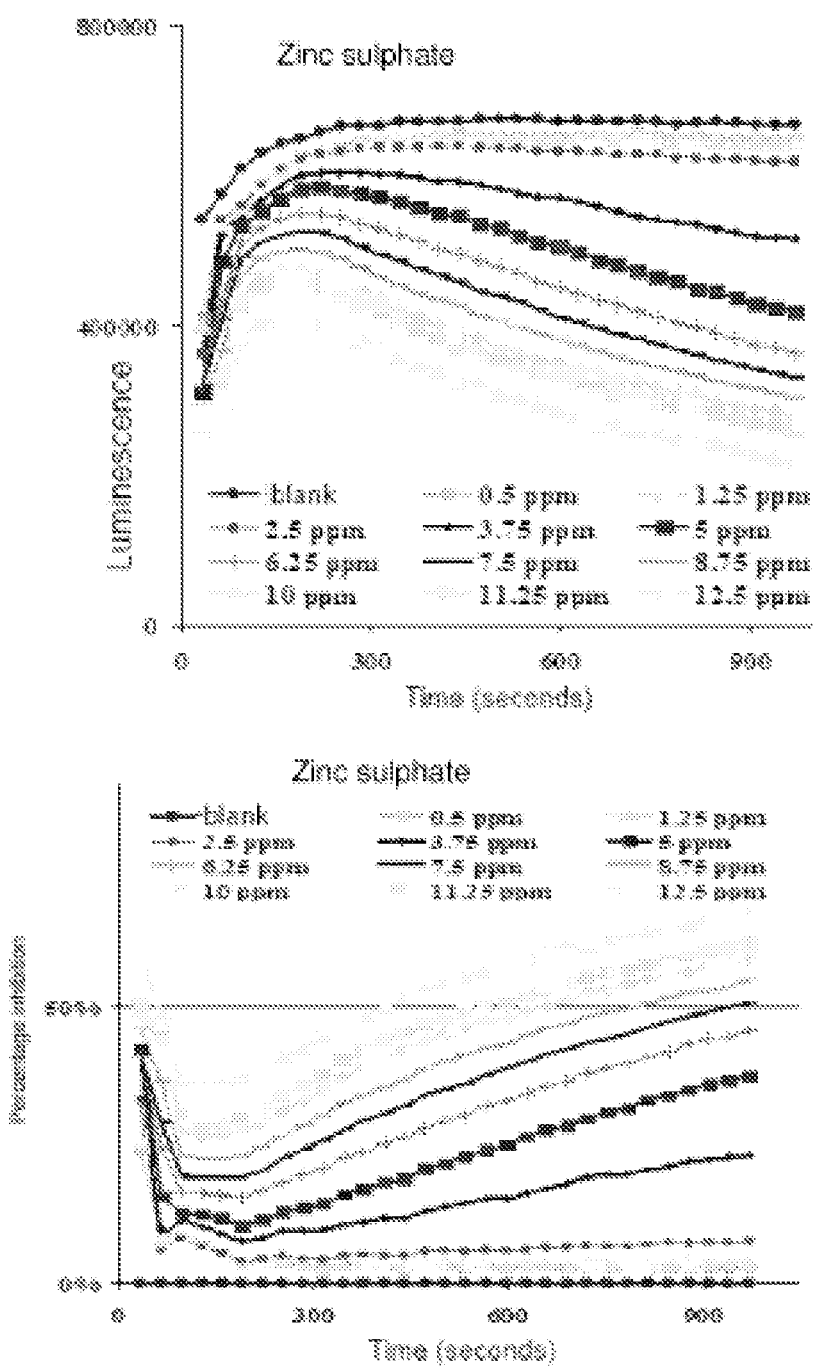

A bacterial lyophilized of *Vibrio fischeri* NRRL B-11177 was resuspended in 5 ml of sterile saline buffer and used to test the toxicity of 11 standard samples of phenol with concentrations increasing from 1 to 25 ppm, with respect to a reference blank. The luminescence in each sample was measured every 30 seconds for the duration of 16 minutes. At the end of the analysis the cuvettes were automatically washed and sterilized. The whole analytical cycle, including washing, was performed in 30 minutes. IC 50 calculated by the analyser resulted to be 18.5 ppm, in perfect agreement with what reported in literature, that is comprised between 13.0 and 26.0 ppm. FIG. 6 shows the luminometric readings in kinetics on the left and the inhibition kinetics upon increasing the phenol concentration on the right. FIG. 7 shows the calculation of IC 50.

Example 2—Toxicity Measurement of Zinc as Reference Heavy Metal

Figure 9:
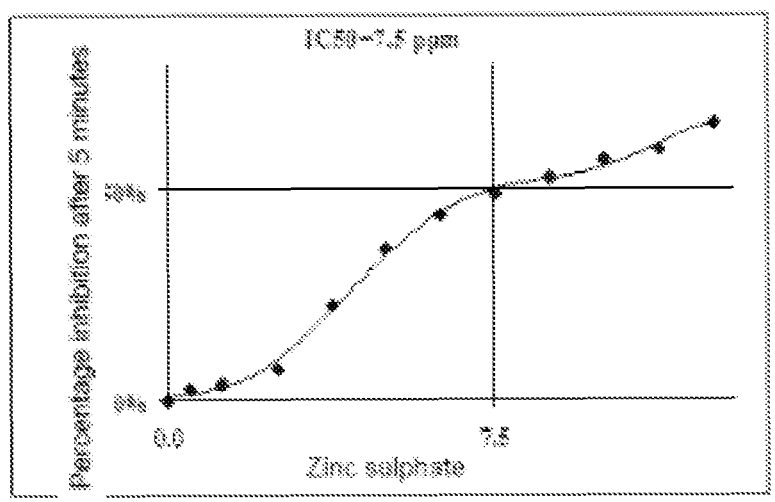
FIG. 9 shows the calculation of IC 50 obtained with the data of FIG. 8.

A bacterial lyophilizate of *Vibrio fischeri* NRRL B-11177, prepared according to original procedure made by the inventor, was resuspended in 5 ml of sterile saline buffer and used to test the toxicity of 11 samples of zinc sulphate with concentrations increasing from 1 to 12.5 ppm, with respect to a reference blank. The luminescence in each sample was measured every 30 seconds for the duration of 16 minutes. At the end of the analysis the cuvettes were automatically washed and sterilized. The whole analytical cycle, including washing, was performed in 30 minutes. IC 50 calculated by the analyzer resulted to be 7.5 ppm, in perfect agreement with what reported in literature, that is comprised between 3 and 10 ppm. FIG. 8 shows the luminometric readings in kinetics on the left and the inhibition kinetics upon increasing the zinc sulphate concentration on the right. FIG. 9 shows the calculation of IC 50.

The invention claimed is:

1. A device based upon random access and discrete technology with direct reading for analysis and monitoring of toxicity in waters using bioluminescent bacteria and microalgae, comprising:
   an aqueous sample storage module;
   an aqueous buffer storage module;
   a dispensing module having three degrees of freedom;
   a reaction tray accommodating reusable, washable and sterilizable reaction cuvettes;
   a reaction cuvette washing and sterilization module coupled with said reaction tray, to wash said reaction cuvettes;
   a controller for controlling modules of the device, comprising hardware and software; and
   one or more luminometric measuring modules arranged at predefined positions of said reaction tray, each luminometric measuring module comprising:
   a photomultiplier coupled to the reaction tray, the photomultiplier having an optical fiber bundle, wherein said optical fiber bundle has i) a rectangular section and a surface substantially corresponding to a surface of a reaction cuvette of said reaction cuvettes on a side of said reaction tray and ii) a round section on a side of said photomultiplier,
   wherein the washing module includes a drain line and a connection to containers, the containers having washing and sterilization solutions,
   wherein the controller is configured to automate analytical cycles, position the reaction cuvettes in front of various detectors arranged along a periphery of the reaction tray, and automatically wash and sterilize the reaction cuvettes, and
   wherein the reaction cuvettes have positions on the reaction tray, and the dispensing module is configured to combine bioluminescent bacteria and/or microalgae with one or more aqueous buffers and one or more samples within the cuvettes in their positions on the reaction tray.

2. The device according to claim 1, further comprising at least one fluorimetric measuring module,
   wherein said fluorimetric measuring module comprises at least three sources of excitation light at different wavelengths, and a respective number of detectors are set at about 90° relative to said light sources, wherein said sources of excitation light are positioned in correspondence of the bottom of the cuvette, and said light sources and detectors are configured to excite the microalgae and measure $IC_{f(t)}$ (%)=$[1-(RVF_{S(t)}/RVF_{B(t)})] \times 100$, wherein $IC_{f(t)}$ (%) is the percentage inhibition at time t, $RVF_{S(t)}$ is the dimensionless measurement of relative variable flurorescence calculated for a sample S at time t, and $RVF_{B(t)}$ is the dimensionless measurement of relative variable flurorescence calculated for a blank B at time t.

3. The device according to claim 1, further comprising a microorganism rehydration module, the rehydration module having
   a basket,
   one or more phials having respective phial plugs, the one or more phials containing lyophilized microorganisms,
   a refrigerated mantle, and
   an automated phial plug extraction device,
   wherein the dispensing module is configured to rehydrate the lyophilized microorganisms housed inside the one or more phials, the one or more phials are housed in the basket, the basket is contained inside the mantle, and the basket is configured to rotate.

4. The device according to claim 2, further comprising a thermostated and lighted reactor for the supporting of algal solutions, the reactor having
   a glass container configured to house the microalgae,
   one or more lights,
   a thermostat,
   a plug, and
   a mixer,
   wherein the mixer is configured to keep the microalgae in suspension, and the controller is configured to control the temperature with the one or more lights, and provide nutritional substance to the microalgae through the dispensing module.

5. The device according to claim 1, further comprising a sampling module.

6. The device according to claim 1, further comprising a colorimetric measuring module arranged at predefined positions of said reaction tray.

7. The device according to claim 1, further comprising channels implemented in the reaction tray, the channels configured to circulate liquid.

8. The device according to claim 3, wherein said microorganisms are bacteria belonging to genus *Photobacterium, Vibrio, Photorhabdus*.

9. The device according to claim 3, wherein said microorganisms are bacteria belonging to genus *Photobacterium, Vibrio, Photorhabdus* and microalgae belonging to species *Chlamydomonas reinhardtii*.

10. The device according to claim 1, wherein the dispensing module further includes a needle having an automatic inner and outer washer and a level sensor.

* * * * *